United States Patent [19]

Kessels

[11] Patent Number: 5,200,555
[45] Date of Patent: Apr. 6, 1993

[54] PROCESS FOR THE PREPARATION OF S(+)-6-METHOXY-α-METHYL-2-NAPHTHALENE-ACETIC ACID

[75] Inventor: Gerard Kessels, Garrucha, Spain

[73] Assignee: Westpur Investment Limited, Douglas, United Kingdom

[21] Appl. No.: 734,598

[22] Filed: Jul. 23, 1991

[30] Foreign Application Priority Data

Jul. 27, 1990 [NL] Netherlands ............ 9001703

[51] Int. Cl.$^5$ .............................. C07B 57/00
[52] U.S. Cl. ........................ 562/401; 562/402; 562/466
[58] Field of Search ................ 562/401, 402, 466

[56] References Cited

U.S. PATENT DOCUMENTS

| | | | |
|---|---|---|---|
| 3,686,183 | 8/1972 | Dyson | 562/401 X |
| 4,752,417 | 6/1988 | Inoue et al. | 562/401 |
| 4,983,765 | 1/1991 | Lukas et al. | 562/401 |
| 5,023,365 | 6/1991 | Giordana et al. | 560/56 |

FOREIGN PATENT DOCUMENTS 0132854 2/1985 European Pat. Off. .

OTHER PUBLICATIONS

*Patent Abstracts of Japan*, vol. 5, No. 164, Oct. 21, 1981 (C-76) (836) & JP 56/95149 (Nisshin Seifun), Aug. 1, 1981.

*Primary Examiner*—José G. Dees
*Assistant Examiner*—Vera C. Clarke
*Attorney, Agent, or Firm*—Lorusso & Loud

[57] ABSTRACT

The invention relates to a process for the preparation of S(+)-6-methoxy-α-methyl-2-naphthalene-acetic acid by resolution of R,S-6-methoxy-α-methyl-2-naphthalene-acetic acid. According to the invention R,S-6-methoxy-α-methyl-2-naphthalene-acetic acid and R(−)-2-amino-1-butanol are dissolved in water at 40°-60° C. Then the solution thus obtained is cooled to 25°-35° C. Subsequently the obtained solution is grafted with a salt of S(+)-6-methoxy-α-methyl-2-naphthalene-acetic acid and R(−)-2-amino-1-butanol, further it is cooled to 5°-15° C. The thereby formed crystals are separated from the solution and washed with water and subsequently hydrolyzed by adding a strong acid, whereby S(+)-6-methoxy-α-methyl-2-naphthalene-acetic acid crystallizes and the obtained crystals are separated from the mother liquor and the R(−)-6-methoxy-α-methyl-2-naphthalene-acetic acid present in the crystallization-mother liquor is racemized by heating, which racemate solution can be reused as starting material.

4 Claims, 1 Drawing Sheet

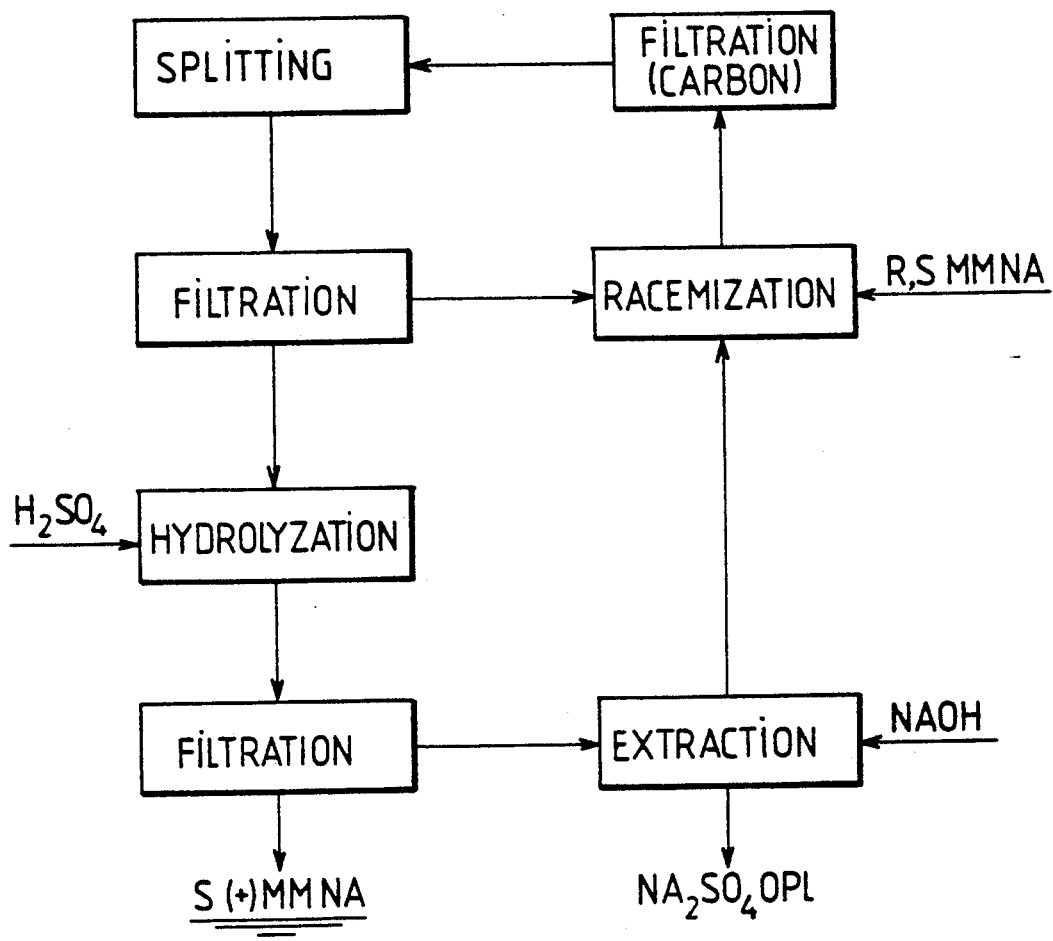

PROCESS FOR THE PREPARATION OF S(+)-6-METHOXY-α-METHYL-2-NAPHTHALENE-ACETIC ACID

The invention relates to a process for the preparation of S(+)-6-methoxy-α-methyl-2-naphthalene-acetic acid by resolution of R,S-6-methoxy-α-methyl-2-naphthalene-acetic acid.

It is noted that for simplicity the compound S(+)-6-methoxy-α-methyl-2-naphthalene-acetic acid will be abbreviated to S(+)M.M.N.A., and the compound R,S-6-methoxy-α-methyl-2-naphthalene-acetic acid will be abbreviated to R,S M.M.N.A.

S(+)M.M.N.A. is an important medicine known by the name of Naproxene. There are a known number of resolution methods of R,S M.M.N.A. which have been used for about 20 years on an industrial scale. It is noted that the S(+)-compound is disproportionately more expensive than the R,S compound. The known resolution methods have the following disadvantages.

One uses optically active bases which are often more expensive.

The optically active bases used for the resolution often have one relatively high molecular weight and so require significant amounts of resolution agent.

The prepared salts normally crystallize very finely so that the separation from the crystallization liquid and the washing of the salt are not easily carried out. Usually a recrystallization is required of the salt to obtain sufficient optical purity.

The resolutions are carried out in solvents. Impurities accumulate in the recrystallization liquid. Good resolutions are difficult to carry out from the impure solutions. When the resolution is to be carried out in a solution this means that the crystallization liquid is quickly made impure and cannot be reused indefinitely.

PRIOR ART

The best known preparation methods of S(+)M.M.N.A. are the resolution of R,S, M.M.N.A. with Cinchonidine and the resolution of R,S M.M.N.A. with S(−)-α-phenyl-ethylamine.

The resolution of R,S M.M.N.A. with Cinchonidine in various variants is described in many patents, e.g. in U.S. Pat. No. 3,683,015 and E.P. 44,984. The resolution with Cinchonidine has the following disadvantages: Cinchonidine is expensive, has a high molecular weight, is toxic, which requires extra precautions in preparing a medicine, the salt of S(+)M.M.N.A. and Cinchonidine crystallizes very finely, causing filtration problems and they have to be prepared in solvents.

The resolution of R,S M.M.N.A. with S(−)-α-phenyl-ethylamine is known from several patents e.g. in E.P. 132,854 and J.P. 8036429.

S(−)-α-phenylethylamine is a rather expensive resolution agent, it has to be crystallized twice to obtain sufficient optical purity and one has to crystallize sometimes from very toxic solvents (for example chloroform).

The invention has the object of providing a new resolution technique whereby the above-mentioned disadvantages of the known resolution methods are efficiently avoided.

Hereto the invention provides a process for the preparation of S(+)-6-methoxy-α-methyl-2-naphthalene-acetic acid by resolution of R,S-6-methoxy-α-methyl-2-naphthalene-acetic acid, characterized in that R,S-6-methoxy-α-methyl-2-naphthalene-acetic acid and R(−)-2-amino-1-butanol are dissolved in water at 40°–60° C., followed by cooling to 25°–35° C., whereafter the obtained solution is grafted with the salt of S(+)-6-methoxy-α-methyl-2-naphthalene-acetic acid and R(−)-2-amino-1-butanol, is further cooled to 5°–15° C. and the so formed crystals are separated from the solution, washed with water and subsequently hydrolyzed by adding a strong acid, whereby S(+)-6-methoxy-α-methyl-2-naphthalene-acetic acid crystallizes and the obtained crystals are separated from the mother liquor, and the R(−)-6-methoxy-α-methyl-2-naphthalene-acetic acid present in the crystallization mother liquor is racemized by heating and the racemization solution may be reused as starting material.

According to the present process R,S M.M.N.A. is resolved by crystallizing a salt of S(+)M.M.N.A. and R(−)-2-amino-1-butanol from an aqueous solution of R,S M.M.N.A. and R(−)2-amino-1-butanol. The great advantages of this method of this invention are: R(−)-2-amino-1-butanol is very cheap as it is a byproduct of the preparation of the medicine Ethambutol; it has a relatively low molecular weight so that relatively little is needed, and it can be recovered and reused. Furthermore it is a stable compound.

Furthermore, it is very attractive that the salt of S(+)M.M.N.A. and R(−)-2-amino-1-butanol formed during the resolution crystallizes in large crystals so as to enable an optically pure product to be obtained by crystallizing only one time.

Also, the resolution is carried out in aqueous medium giving a great advantage.

After a resolution one wishes preferably in the crystallization mother liquor to directly racemize the solved, non-desired enantiomer and subsequently, after adding a new portion of R,S-compound and the recovered resolving agent, to reuse the solution for a following crystallization and to repeat this indefinitely.

It has appeared that the resolutions of R,S M.M.N.A. by crystallization with an optically active base are very sensitive towards impurities with the crystallization liquid.

When crystallizing from a impure liquid, said crystallization will be retarded and the crystals remain small and poor optical purity is reached whereby recrystallization of the formed salt is required.

When the resolution is to be carried out in a solvent, decomposition products and technical impurities accumulate therein whereby the solutions cannot be often reused. Because the process of the invention is carried out in aqueous medium, the decomposition products and technical impurities can be easily removed from the aqueous solution by filtration with active carbon whereby the solution can be used practically indefinitely. One does not have this possibility when using solvents.

It is noted that the German patent 2,008,272 in general terms indicates that R(−)-2-amino-1-butanol besides 36 other optical active bases, is suitable for the resolution of R,S M.M.N.A. by crystallization of the salt of S(+)M.M.N.A. and R(−)-2-amino-1-butanol from solvents. This document does not discuss crystallization from an aqueous solution.

The said patent does not give any data and does not give an example directed to the specific use of R(−)-2-amino-1-butanol. It has also appeared that in the solvents mentioned in the respective patent a good solution of R,S M.M.N.A. with R(−)-2-amino-1-butanol is not possible because the salt of S(+)-M.M.N.A. and R(−)-2-amino-1-butanol and also a portion of the salt of R(−) M.M.N.A. and R(−)-2-amino-1-butanol crystallizes. There is no sufficient selectivity in the solvents to obtain an optically pure product.

As mentioned earlier, the invention crystallizes from an aqueous solution wherein the salts of S(+)M.M.N.A. and R(−) M.M.N.A. with R(−)-2-amino-1-butanol are sufficiently different in solubility to enable resolution.

In the patent IT 2,368,984 a method is described wherein e.g. R(−)-2-amino-1-butanol also is used. For the resolution the amide of S(+)M.M.N.A. and R(−)-2-amino-1-butanol is crystallized. This is different from a simply formed and hydrolyzed salt of S(+)M.M.N.A. and R(−)-2-amino-1-butanol. This means that several extra chemical syntheses have to be carried out.

So the acid chloride of an ester has to be made from R,S M.M.N.A., subsequently the amide has to be formed with R(−)-2-amino-1-butanol and after the resolution the amide has to be hydrolyzed.

In the process of the invention the salt of S(+)M.M.N.A. and R(−)-2-amino-1-butanol is formed spontaneously in the aqueous medium and the obtained salt is simply hydrolyzed in aqueous medium with a strong acid.

Now the process of the invention is further explained.

First a solution is made from R,S M.M.N.A. and R(−)-2-amino-1-butanol in warm water at 40°-60° C. in a nearly equimolar proportion. Subsequently, the so obtained solution is slowly cooled to 25°-35° C. At the temperature at which the saturation point is reached, the solution is grafted with the salt of S(+)M.M.N.A. and R(−)-2-amino-1-butanol. By further cooling the solution to 5°-15° C. the salt of S(+)M.M.N.A. and R(−)-2-amino-1-butanol begins to crystallize. It has appeared to be important that crystallizing is such that no large oversaturation of the solution takes place since in such a case also the salt of the R(−) enantiomer appears to crystallize whereby the required good optical purity is not obtained.

It has appeared that sufficient grafting is required whereas cooling of the solution should occur slowly and uniformly.

It has appeared to be possible to replace a portion of the R(−)-2-amino-1-butanol by another base like NaOH or KOH. By adding another base it has appeared that the salt of the undesired enantiomer crystallizes less quickly and a higher productivity of the resolution can be obtained.

After the end of the crystallization the formed crystals, large needles, are separated from the liquid by filtration and washed with water.

The separated salt subsequently is solved in warm water and hydrolyzed by adding a strong acid for example sulphuric acid whereby S(+)M.M.N.A. crystallizes which subsequently is separated by filtration from the mother liquor.

In the hydrolysis-mother liquor the sulphate of R(−)-2-amino-1-butanol is present in solution which can be extracted from the solution by a suitable solvent after making alkaline the liquid.

In the crystallization-mother liquor, a portion of the salt of R,S M.M.N.A. and R(−)-2-amino-1-butanol and the salt of R(−)M.M.N.A. and R(−)-2-amino-1-butanol are resolved. The R(−)M.M.N.A. can be directly racemized in the crystallization-mother liquor to S M.M.N.A. by heating. In aqueous medium the racemization speed is rather low. By adding an alcohol the racemization speed can be considerably increased whereby the racemization temperature can be lower and the racemization time shorter.

After the racemization the added alcohol is distilled. The remaining solution of R,S M.M.N.A. and R(−)-2-amino-1-butanol is now purified by filtration with active carbon whereby it is possible to reuse the solution practically indefinitely for crystallization after adding a new portion of R,S M.M.N.A. and the R(−)-2-amino-1-butanol recovered from the hydrolysis-mother liquor.

The above described method is schematically represented by the drawing.

BRIEF DESCRIPTION OF THE DRAWING

FIG. 1. The Figure shows a schematic representation of the method used in the resolution R,S M.M.N.A into the component S(+) M.M.N.A.

DETAILED DESCRIPTION OF THE DRAWING

In the initial step, R,S M.M.N.A. is resolved with R(−)-2-amino-1 butanol followed by carbon filtration. The resolution step results in the crystallization of the salt of S(+) M.M.N.A and R(−)-2-amino-1-butanol which crystals are then separated from the liquid by filtration. Hydrolysis of the crystals follows by the addition of a strong acid whereby S(+) M.M.N.A crystallizes. The hydrolyzed crystals are then separated by filtration from the mother liquor which contains residual components which can then be reused in the initial step of this process.

Finally the present invention is further explained by the following non-limiting examples.

EXAMPLE I

In a flask, of 100 cm$^3$, 60 cm$^3$, of water 12 g of R,S-M.M.N.A. and 4.8 g of R(−)-2-amino-1-butanol were transferred and mixed.

The obtained mixture was heated to about 50° C., to dissolve R,S- M.M.N.A. The mixture was slowly cooled to about 30° C.

At this temperature 0.2 g of finely ground salt of S(+)M.M.N.A. and R(−)-2-amino-1-butanol were added.

After grafting recrystallization took place whereafter the mixture during 5 hours under stirring was uniformly cooled to about 10° C. It was stirred for an hour at about 10° C. whereafter the crystals were filtered and washed on the filter with little water at about 0° C.

The obtained crystals were dissolved in 40 cm$^3$ of water of about 60° C. Now under stirring 20% concentrated sulphuric acid was added until a pH of about 1 was reached. During the addition of diluted sulphuric acid the product crystallized. The mixture was cooled to about 25° C. and the crystallized product was filtered, washed with water and dried.

1.9 g of white crystalline substance was obtained. The specific rotation was: α20/D +62 (C=1% in chloroform).

EXAMPLE II

Crystallization

In a flask of 500 cm$^3$ the following were mixed: 280 cm$^3$ of water, 2.8 g of NaOH and 22 g of R(−)-2-amino-1-butanol. The so obtained mixture was heated to about 55° C., whereafter 67.5 g of R,S M.M.N.A. were added. After obtaining a solution the same was cooled to about 32° C. At this temperature the solution was grafted with 1.5 g of very finely ground salt of S(+)M.M.-N.A. and R(−)-2-amino-1-butanol. After grafting the crystallization began. Subsequently, under agitation during 7 hours the temperature was decreased to about 6° C. For 2 hours agitation continued at about 6° C. and the formed crystals were filtered and washed with a little cold water.

Hydrolysis of the obtained salt

The obtained salt was dissolved in 225 cm$^3$ of water of about 60° C. 20% sulphuric acid was added and stirred at 60°–70° C. for about 2 hours until a pH lower than 1.5 was obtained. Now the solution was cooled to about 25° C. and the white crystalline substance crystallized during the addition of the dilute sulphuric acid which was then filtered, washed with water and dried.

Hereby 17.4 g of a white crystalline product was obtained. The obtained product at analysis appeared to have a specific rotation of $\alpha 20/D: +63.8$ (C=1 in chloroform).

Recovering of R(−)-2-amino-1-butanol

In the mother liquor of the foregoing hydrolysis, (the foregoing step) the sulphate of R(−)-2-amino-1-butanol was dissolved. 8 g of NaOH was added to the hydrolysis mother liquor under stirring and this was followed by a solution about 35 g of NaCl was. After dissolution of the NaCl the obtained solution of extracted five times in a separation funnel each time with 40 cm$^3$ of isobutyl alcohol.

The collected extracts, in total 192 cm$^3$, were evaporated in a rotating vacuum drier.

A distillation residue, the recovered R(−)-2-amino-1-butanol, was obtained in an amount of about 6.1 g.

The product appeared to have a specific rotation of: $\alpha 20/D: -15.8$ (C=1 in 1N hydrochloric acid).

Racemization

A crystallized mixture of R,S M.M.N.A., R(−)M.M.N.A. and R(−)-2-amino-1-butanol is present in the mother rye in the dissolved state.

To the crystallization-mother liquor (+wash water), in total 335 40 cm$^3$, 335 cm$^3$ of tertiary butanol were added and the obtained mixture about 22 hours at about 140° C. After cooling the mixture a sample of about 5 cm$^3$ was taken, diluted with about 20 cm$^3$ water and acidified to a pH of about 1 with 20% sulphuric acid whereby a white crystalline product R,S M.M.N.A. was obtained.

After filtering, washing with water and drying the specific rotation was determined. The $\alpha 20/D$ was 0.3 which means that the racemization was nearly complete. Subsequently the racemization mixture in a flask of 1 l was provided with a spike mount and distillation cooler, subjected to distillation until the boiling temperature of the mixture in the flask was higher than about 99° C.

Then the remaining aqueous racemization liquid in the flask was cooled to about 25° C. and the 6.1 g of recovered R(−)-2-amino-1-butanol was added. Subsequently 4 g active carbon was added whereafter stirring was continued for 15 minutes. Thereafter the active carbon was separated by filtration from the mixture. The now almost colourless solution was supplemented with a little water to a volume of 330 cm$^3$. This liquid was reused for a following crystallization.

EXAMPLE III

In a flask of 500 cm$^3$ the 330 cm$^3$ purified racemic liquid was stirred together with the addition of the recovered R(−)-2-amino-1-butanol.

The liquid was heated to about 55° C., whereafter a mixture of 0.2 g of NaOH, 1.1 g R(−)-2-amino-1-butanol and 17.0 g of R,S M.M.N.A was added. Stirring was continued until a solution was obtained which subsequently was cooled to about 32° C. Subsequently grafting was done and crystallization like in Example II. The resolution can practically be repeated indefinitely.

I claim:

1. A process for the preparation of S(+)-6-methoxy-α-methyl-2-naphthalene-acetic acid by resolution of R,S-6-methoxy-α-methyl-2-naphthalene-acetic acid comprising
    a) dissolving R,S-6-methoxy-α-methyl-2-naphthalene-acetic acid, R(−)-2-amino-1-butanol and water at 40°–60° C. to obtain a solution,
    b) cooling the solution of (a) to 25°–35° C.,
    c) grafting the cooled solution by adding a salt of S(+)-6-methoxy-α-methyl-2-naphthalene-acetic acid and R(−)-2-amino-1-butanol,
    d) cooling the solution of (c) to 5°–15° C. forming crystals, e) separating by filtration the formed crystals from the solution of (d),
    f) washing the formed crystals of (e) with water,
    g) hydrolyzing said formed crystals by adding strong acid to obtain hydrolyzed crystals of S(+)-6-methoxy-α-methyl-2-naphthalene-acetic acid and residual mother liquor,
    h) separating by filtration the hydrolyzed crystals from the mother liquor,
    i) racemizing the residual components present in the liquor by heating the mother liquor of (h),
    j) repeating the process beginning with step (a) by using the recycled residual components of (i).

2. The method of claim 1 wherein the strong acid in the hydrolysis step g is H$_2$SO$_4$.

3. The method of claim 1 wherein a mixture of R(−)-2-amino-1-butanol and a base is substituted for R(−)-2-amino-1-butanol.

4. The method of claim 1 wherein a mixture of R(−)-2-amino-1-butanol and a base selected from the group consisting of NaOH, KOH, and mixture thereof is substituted for R(−)-2-amino-1-butanol.

* * * * *